US00PP16921P2

(12) United States Plant Patent
Andrusiv

(10) Patent No.: US PP16,921 P2
(45) Date of Patent: Aug. 1, 2006

(54) ***BERBERIS* PLANT NAMED 'ADMIRATION'**

(50) Latin Name: *Berberis thunbergii*
Varietal Denomination: Admiration

(76) Inventor: Michal Andrusiv, J. Metyse 1079, 570 07 Litomysl (CS)

( * ) Notice: Subject to any disclaimer, the term of this patent is extended or adjusted under 35 U.S.C. 154(b) by 77 days.

(21) Appl. No.: 11/053,251

(22) Filed: Feb. 7, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para

(57) ABSTRACT

A new cultivar of *Berberis* plant named 'Admiration' that is characterized by broad upright habit, orange-red foliage with yellow margins, and absence of flowers. In combination these traits set 'Admiration' apart from all other existing varieties of *Berberis* known to the inventor.

2 Drawing Sheets

Genus: *Berberis.*
Species: *thunbergii.*
Denomination: Admiration.

BACKGROUND OF THE INVENTION

The present invention relates to a new and distinct cultivar of barberry that is grown as a dwarf shrub for container or landscape. The new cultivar is known botanically as *Berberis thunbergii* and will be referred to hereinafter by the cultivar name 'Admiration'.

'Admiration' was selected by the inventor in Litomysl, The Czech Republic in 1994, for unique foliage color. The new cultivar 'Admiration' is a hybrid plant that resulted from directed cross-pollination conducted by the inventor in a cultivated area of Litomysl, The Czech Republic. Cross-pollination was between an individual plant of *Berberis thunbergii* 'Goldalita' (unpatented) and an individual plant of *Berberis thunbergii* 'Atropurpurea' (unpatented). The female parent is *Berberis thunbergii* 'Goldalita' and the male parent is *Berberis thunbergii* 'Atropurpurea'.

The new *Berberis* variety 'Admiration' is a deciduous dwarf shrub characterized by orange-red foliage with yellow margins. This foliage color continues throughout the summer season. There are no dwarf *Berberis,* known to the inventor, that exhibit this foliage color. To date the inventor has observed no flowers produced by 'Admiration'. The foliage color and absence of flowers distinguish 'Admiration' from all other *Berberis* known to the inventor.

'Admiration' differs from the parent plants in that female parent plant 'Goldalita' is yellow and male parent 'Atropurpurea' is deep reddish brown while 'Admiration' has orange-red foliage with yellow margins. The two closest varieties known to the inventor are *Berberis thunbergii* 'Nana' (unpatented) and *Berberis thunbergii* 'Bagatelle' (unpatented). The foliage of 'Nana' is deeper reddish brown and 'Admiration' has the yellow margin with brighter orange centers. 'Bagatelle' is more compact than 'Admiration' and also does not have the yellow margin.

The first asexual reproduction of 'Admiration' was conducted by the inventor in 1995, in a cultivated area of Litomysl, The Czech Republic. The method used for asexual propagation was vegetative cuttings. Since that time the distinguishing characteristics of 'Admiration' have been determined stable and have reproduced true to type in successive generations.

An application for European Community Plant Variety Rights was filed Apr. 22, 2003, Ser. No. 2003/0741. The first sale or distribution to the public of any plants of 'Admiration' occurred on or after Mar. 1, 2004.

SUMMARY OF THE INVENTION

The following traits have been repeatedly observed and represent the characteristics of the new *Berberis* cultivar 'Admiration'. These traits in combination distinguish 'Admiration' from all other commercial varieties of *Berberis* known to the inventor. 'Admiration' has not been tested under all possible conditions and phenotypic differences may be observed with variations in environmental, climatic and cultural conditions, without however, any variance in genotype.

1. *Berberis* 'Admiration' is a deciduous shrub.
2. *Berberis* 'Admiration' is suitable for use in containers or the landscape.
3. To date *Berberis* 'Admiration' has not produced flowers.
4. *Berberis* 'Admiration' exhibits a broad upright habit.
5. *Berberis* 'Admiration' exhibits red-orange foliage with yellow margins.
6. *Berberis* 'Admiration' is propagated using vegetative cuttings.
7. *Berberis* 'Admiration' is hardy to USDA Zone 5.
8. *Berberis* 'Admiration' is 27 cm. in width and 18 cm. in height in a 2-liter container.

BRIEF DESCRIPTION OF THE DRAWINGS

The accompanying color drawings illustrate the overall appearance of the new cultivar 'Admiration' showing the colors as true as it is reasonably possible to obtain in colored reproductions of this type. The drawings were made in September. The plants shown in the drawings are 2-yearsold in 2 liter containers, and were grown out-of-doors in Boskoop, The Netherlands. Daytime temperatures ranged from 15° Centigrade to 30° Centigrade. Nighttime temperatures ranged from 7° Centigrade to 14° Centigrade. The light was normal outdoor light level. No photoperiodic treatments and no growth retardants were applied to the plants. Colors in the drawings may differ from the color values cited in the detailed botanical description, which accurately describe the actual colors of the new variety of *Berberis* named 'Admiration'.

The drawing labeled as FIG. 1 depicts the entire plant from a side perspective.

Figure 1:
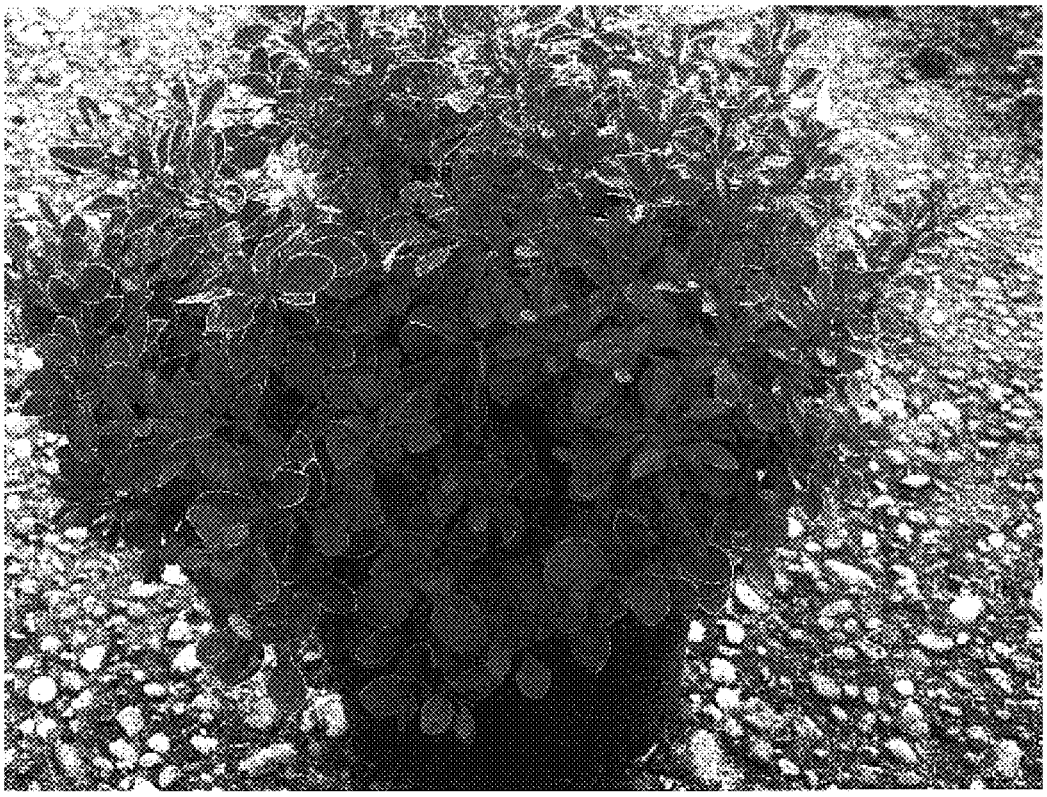
Figure 2:
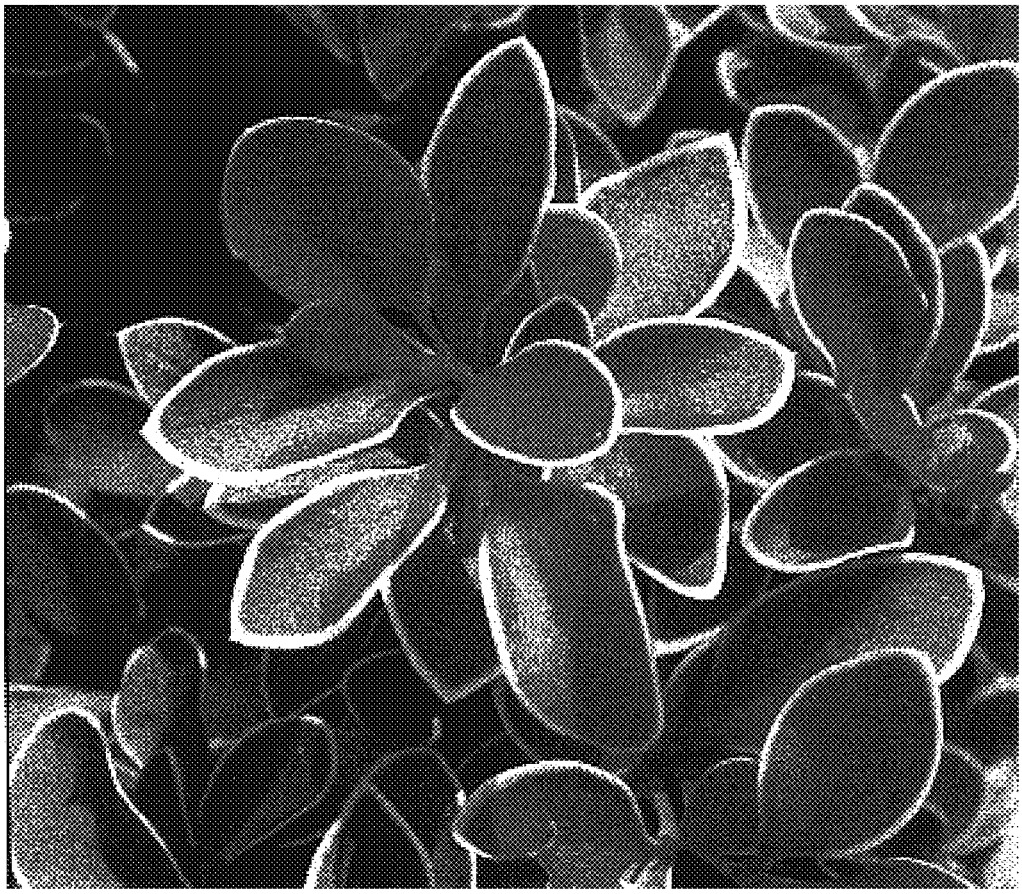

The drawing labeled as FIG. 2 depicts a close-up view of the foliage.

Drawings were made using conventional techniques and although colors may appear different from actual colors due to light reflectance they are as accurate as possible by conventional photography.

BOTANICAL DESCRIPTION OF THE PLANT

The following is a detailed description of 'Admiration' as grown in a 2-liter containers, out-of-doors in Boskoop, The Netherlands. The color determinations are in accordance with The 2002 Royal Horticultural Society Colour Chart of The Royal Horticultural Society, London, England, except where general color terms of ordinary dictionary significance are used. The growing requirements are similar to the species.

Botanical classification:
- *Genus.*—*Berberis.*
- *Species.*—*thunbergii.*
- *Denomination.*—'Admiration'.

Commercial classification: Deciduous shrub.

Use: Plant for use in containers or landscape.

Common name: Barberry.

Commercial container size: For liner production, a 5 cm round or square plug or cell or container; for planting in the garden or landscape, a "nursery 1 gallon" or equivalent or larger.

Cultural requirements: Plant in full sun to light shade in well-drained soil with moderate to regular water.

Parentage: *Berberis* 'Admiration' is a hybrid plant that resulted from direct cross-pollination of the following parents:
- *Female parent plant.*—An individual plant of *Berberis thunbergii* 'Goldalita'.
- *Male parent plant.*—An individual plant of *Berberis thunbergii* 'Atropurpurea'.

Plant description:
- *Bloom period.*—None. Plant has not bloomed to date.
- *Plant habit.*—Broad upright habit.
- *Overall plant shape.*—Flattened globular.
- *Vigor.*—Low to moderate vigor.
- *Root system.*—Fibrous roots.
- *Plant dimensions.*—27 cm. in width and 18 cm. in height in a 2-liter container.
- *Growth rate.*—An average of 6 cm. per season until mature.
- *Hardiness.*—USDA Zone 5.
- *Propagation.*—Propagation is accomplished using vegetative cuttings.
- *Rooting time.*—An average of 6 weeks is needed for an initial cutting to develop roots.
- *Crop time.*—24 months are needed to produce a commercial 2-liter container from a rooted cutting.
- *Special growing considerations.*—Pinching back improves branching.
- *Disease resistance and susceptibility.*—Not more susceptible to pests and diseases than other *Berberis thunbergii* cultivars known to the inventor.
- *High temperature tolerance.*—Not tested in higher however it is likely to be tolerant of temperatures up to 35° Centigrade.

Stem:
- *Stem color* (*immature stems*).—N34A.
- *Stem color* (*mature stems*).—Color ranges from 200A to N200A.
- *Basal stem dimensions.*—5 cm. in length and 0.50 cm. in diameter.
- *Stem surface.*—Surface of stems ranges from glabrous to furrowed on an individual plant.
- *Internode length.*—1–2 cm. between nodes.
- *Branching habit.*—Basal branching with free branching lateral stems.
- *Number of lateral branches.*—An average of 80 lateral branches.
- *Lateral branch length.*—An average of 8 cm. in length.
- *Lateral branch diameter.*—An average of 1.2 mm. in diameter.
- *Internode length.*—An average of 6 mm. between nodes.
- *Stem shape.*—Cylindrical.
- *Stem surface.*—Mature stems are slightly ribbed while immature stems are glabrous and glossy.
- *Stem strength.*—Moderate in strength.
- *Stem pubescence.*—None present.
- *Stipules, tendrils, thorns or spines.*—Thorns present.
- *Thorn length.*—Thorns range in length from 4–6 mm.
- *Thorn apex.*—Acuminate.
- *Thorn surface.*—Glabrous.
- *Thorn base.*—Truncate.
- *Thorn color.*—Individual colors N167A and N199B are both present on an individual plant.

Foliage:
- *Type.*—Deciduous.
- *Arrangement.*—Alternate.
- *Durability of leaf to stress.*—Moderate to high.
- *Shape.*—Obovate.
- *Margins.*—Entire; with either green-yellow edge, 1A, or a more prominent margin on adaxial surface, same color, up to 1 mm in width.
- *Division.*—Simple.
- *Apex.*—Individual leaf apices range from mucronulate to abruptly acute.
- *Base.*—Elongated attenuate.
- *Pubescence* (*adaxial and abaxial surfaces*).—None present.
- *Leaf surface* (*abaxial and adaxial surfaces*).—Glabrous.
- *Leaf appearance* (*adaxial and abaxial surfaces*).—Slightly glossy.
- *Quantity of leaves per lateral branch.*—An average of 50 leaves per lateral branch.
- *Leaf length.*—Individual leaves are an average of 2.1 cm. in length.
- *Leaf width.*—Individual leaves are an average of 1.2 cm. in width.
- *Leaf attachment.*—Sessile.
- *Petioles.*—None present.

*Immature leaf color* (*adaxial surface*).—Individual colors N34A, 151B and 151C are present on an individual leaf.

*Immature leaf color* (*abaxial surface*).—Individual colors 182B, 151B and 151C are present on an individual leaf.

*Mature leaf color* (*adaxial surface*).—A range of individual colors N34A, 183A, 183B, 151C and 143A are present on an individual plant.

*Mature leaf color* (*abaxial surface*).—A range of individual colors 182B, 191A, 151C, 191A and 138B are present on an individual plant.

*Venation.*—Pinnate.

*Vein color on adaxial surface* (*immature leaf*).—N34A.

*Vein color on abaxial surface* (*immature leaf*).—182B.

*Vein color on adaxial surface* (*mature leaf*).—A range of individual vein colors N34A, 183A, 183B and 143A are present on an individual plant.

*Vein color on abaxial surface* (*mature leaf*).—A range of individual vein colors 182B, 191A, 191A and 138B are present on an individual plant.

*Fragrance.*—None.

Flowers, reproductive organs and seed: 'Admiration' has not flowered to date.

What is claimed is:

1. A new and distinct cultivar of *Berberis* plant named 'Admiration', as described and illustrated herein.

* * * * *